US012463001B2

(12) United States Patent
Martin et al.

(10) Patent No.: US 12,463,001 B2
(45) Date of Patent: Nov. 4, 2025

(54) ISOTHERMAL ION SOURCE WITH AUXILIARY HEATERS

(71) Applicant: SHINE Technologies, LLC, Janesville, WI (US)

(72) Inventors: Daniel Martin, Janesville, WI (US); Joseph Sherman, Santa Fe, NM (US); Sarko Cherekdjian, Janesville, WI (US)

(73) Assignee: SHINE Technologies, LLC, Janesville, WI (US)

( * ) Notice: Subject to any disclaimer, the term of this patent is extended or adjusted under 35 U.S.C. 154(b) by 259 days.

(21) Appl. No.: 18/255,732

(22) PCT Filed: Dec. 7, 2021

(86) PCT No.: PCT/US2021/062174
§ 371 (c)(1),
(2) Date: Jun. 2, 2023

(87) PCT Pub. No.: WO2022/125528
PCT Pub. Date: Jun. 16, 2022

(65) Prior Publication Data

US 2024/0047165 A1 Feb. 8, 2024

Related U.S. Application Data

(60) Provisional application No. 63/122,699, filed on Dec. 8, 2020.

(51) Int. Cl.
*H01J 27/22* (2006.01)
*A61N 1/44* (2006.01)

(52) U.S. Cl.
CPC ................ *H01J 27/22* (2013.01); *A61N 1/44* (2013.01)

(58) Field of Classification Search
CPC .................................. H01J 27/22; A61N 1/44
See application file for complete search history.

(56) References Cited

U.S. PATENT DOCUMENTS 3,296,481 A 1/1967 Peters
3,825,790 A 7/1974 Bacal et al.
(Continued)

FOREIGN PATENT DOCUMENTS

CN 108411273 A 8/2018
JP 61-032940 2/1986
(Continued)

OTHER PUBLICATIONS

Farley et al., "Freeman and Bernas Ion Sources", The Physics and Technology of Ion Sources, Aug. 25, 2004, pp. 133-161.
(Continued)

*Primary Examiner* — Srinivas Sathiraju
(74) *Attorney, Agent, or Firm* — Foley & Lardner LLP

(57) ABSTRACT

An ion source includes a chamber having a first end, a second end opposite the first end, a first wall extending from the first end to the second end, and a second wall opposite the first wall. The ion source also includes a source filament at the first end of the chamber and configured to emit electrons and a first amount of heat, a beam aperture at the second wall of the chamber, and one or more heaters positioned within the chamber and between the second end and the beam aperture and operable to provide a second amount of heat. The one or more heaters are positioned and operable such that the second amount of heat balances the first amount of heat to reduce or eliminate a temperature gradient in the chamber.

20 Claims, 9 Drawing Sheets

(56) References Cited

U.S. PATENT DOCUMENTS 4,616,157 A 10/1986 Naylor et al.
5,036,252 A * 7/1991 Lob ........................ H01J 27/16 315/111.41
6,356,026 B1 3/2002 Murto
6,602,714 B1 * 8/2003 Tagge .................... G01N 31/10 73/54.23
7,435,971 B2 10/2008 Vanderberg et al.
7,819,981 B2 10/2010 Dimeo et al.
7,834,554 B2 11/2010 Horsky
7,960,709 B2 6/2011 Horsky et al.
8,154,210 B2 4/2012 Horsky et al.
8,368,309 B2 2/2013 Horsky et al.
8,809,800 B2 * 8/2014 Koo .................... H01J 37/3171 250/424
9,142,379 B2 9/2015 Koo et al.
10,037,883 B2 7/2018 Chebi et al.
10,390,877 B2 * 8/2019 Heggeness ........... A61B 17/025
10,504,682 B2 12/2019 Chang et al.
11,170,973 B2 * 11/2021 Patel ....................... H01J 37/08
11,430,627 B2 * 8/2022 Tootell ...................... H01J 1/28
11,471,210 B2 * 10/2022 Pellegrino ................. A61F 7/00
11,664,192 B2 * 5/2023 Patel ....................... H01J 37/08 315/326
11,764,026 B2 * 9/2023 Tootell .................. H01J 27/205 250/427
11,830,637 B2 * 11/2023 Piefer ...................... G21B 1/01
11,854,760 B2 * 12/2023 Wright .................... H01J 27/22
12,059,193 B2 * 8/2024 Pellegrino .............. A61B 18/14
2003/0089847 A1 * 5/2003 Guevremont ........ G01N 27/624 250/282
2003/0218429 A1 11/2003 Kinoyama
2008/0006099 A1 * 1/2008 Baumgardner ....... B01L 3/5027 422/82.12
2008/0048107 A1 * 2/2008 Mcewen ............... H01J 49/107 250/282
2009/0014667 A1 1/2009 Hahto et al.
2009/0032727 A1 * 2/2009 DiVergilio .............. H01J 37/08 250/423 R
2009/0090862 A1 * 4/2009 Kawana .............. H01J 49/0468 250/288
2009/0206275 A1 * 8/2009 Henley ............... H01J 37/3171 250/492.1
2010/0024841 A1 * 2/2010 Koo ........................ H01J 27/14 134/1.1
2010/0107980 A1 * 5/2010 Horsky ................. H01J 27/024 315/111.81
2013/0084408 A1 4/2013 Nakao et al.
2013/0189594 A1 * 7/2013 Breit ...................... B64D 11/04 165/41
2013/0209901 A1 * 8/2013 Breit ................. H01M 8/04074 429/410
2014/0183957 A1 * 7/2014 Duchesneau ......... F01K 13/006 307/64
2014/0319369 A1 10/2014 Koo et al.
2015/0011096 A1 1/2015 Chandrasekharan et al.
2020/0294751 A1 * 9/2020 Tootell .................... H01J 49/08
2021/0110995 A1 * 4/2021 Patel ..................... H01J 37/302
2021/0118661 A1 * 4/2021 Corkum .............. H01J 49/0463
2021/0213454 A1 * 7/2021 Jones ........................ H05B 3/26
2022/0021290 A1 * 1/2022 Mills ....................... H02S 10/30
2022/0223398 A1 * 7/2022 Corkum .............. H01J 49/0463
2022/0232692 A1 * 7/2022 Piefer ...................... H05H 3/06
2022/0270775 A1 * 8/2022 Piefer ...................... G21G 1/08
2023/0028580 A1 * 1/2023 Tootell .................... H01J 49/08
2023/0138303 A1 * 5/2023 Pellegrino ................. A61F 7/00 600/407
2023/0238154 A1 * 7/2023 Thompson ............... G21B 1/05 376/100
2024/0047165 A1 * 2/2024 Martin .................... H01J 27/22
2024/0299077 A1 * 9/2024 Pellegrino .............. A61N 5/045
2024/0381520 A1 * 11/2024 Gribb ....................... H05H 1/54

FOREIGN PATENT DOCUMENTS

JP 01-095455 4/1989
JP 2003-346672 12/2003
JP 2004-234929 8/2004

OTHER PUBLICATIONS

'Structure of Ion Source', Shimadzu.com, Feb. 1, 2022 (Feb. 1, 2022, date retrieved) 3 [retrieved from the internet on Feb. 1, 2022 (Feb. 1, 2022) at <https://www.ssi.shimadzu.com/productslgas-chromatography-massspectrometry/structure_of_ionsource.html>] para 1.

International Search Report and Written Opinion for PCT/US2021/062174 dated Feb. 1, 2022, 12 pages.

* cited by examiner

ISOTHERMAL ION SOURCE WITH AUXILIARY HEATERS

CROSS-REFERENCE TO RELATED APPLICATIONS

This application is a 371 U.S. National Stage Application of International Application No. PCT/US2021/062174 filed Dec. 7, 2021, which claims the benefit of and priority to U.S. Provisional Patent Application No. 63/122,699 filed Dec. 8, 2020, the entire disclosures of which are incorporated by reference herein.

BACKGROUND

The present disclosure relates generally to the field of heavy metal ion production, for example production of heavy metal ions used in health care applications. More specifically, the present disclosure relates to improving the efficiency and overall operation of ion sources, for example ion sources for production of heavy metal ions such as Ytterbium-176.

SUMMARY

One implementation of the present disclosure is an ion source. The ion source includes a chamber having a first end, a second end opposite the first end, a first wall extending from the first end to the second end, and a second wall opposite the first wall. The ion source also includes a source filament at the first end of the chamber, and the ion source configured to emit electrons and a first amount of heat, a beam aperture at the second wall of the chamber, and one or more heaters positioned within the chamber and between the second end and the beam aperture and operable to provide a second amount of heat. The term "aperture" can refer to an opening of any shape, for example a slot, slit, rectangular opening, circular opening, or opening of some other shape. The one or more heaters are positioned and operable such that the second amount of heat balances the first amount of heat to reduce or eliminate a temperature gradient in the chamber.

In some embodiments, the ion source also includes a plurality of thermocouples distributed in the chamber and a controller. The controller is configured to provide closed-loop control of the one or more heaters based on output from the plurality of thermocouples.

In some embodiments, the ion source also includes a reflector electrode at the second end of the chamber and configured to reflect the electrons away from the second end. Operation of the one or more heaters may reduce or eliminate condensation on an insulator of the reflector electrode.

In some embodiments, a gas inlet is provided at the first wall of the chamber. The gas inlet may be aligned with the beam aperture. The one or more heaters may include a first cylindrical heater extending from the second end of the chamber and along the second wall of the chamber. The one or more heaters may include a second cylindrical heater extending from the second end of the chamber and along the second wall of the chamber. The second cylindrical heater may be spaced apart from the first cylindrical heater.

In some embodiments, the ion source also includes a plurality of support posts coupled to the first wall of the chamber and extending away from the chamber. The plurality of support posts may provide uniform pathways for heat transfer out of the chamber. The ion source may also include a water-cooling system. The support posts extend from the chamber to the water-cooling system which is configured to remove heat from the plurality of support posts. The water-cooling system may be further configured to measure the heat removed from the plurality of support posts by the water-cooling system.

In some embodiments, the ion source includes an oven configured to provide an Ytterbium gas into the chamber via an inlet in the second wall.

In some embodiments, the ion source includes a test device configured to measure a plasma uniformity of an ion beam emitted from the beam aperture. Control for the one or more heaters is tuned based on the plasma uniformity.

In some embodiments, the second amount of heat is substantially equal to the first amount of heat. Reducing or eliminating the temperature gradient in the chamber may cause a reduction or elimination of a non-uniform current in an ion beam emitted from the beam aperture.

Another implementation of the present disclosure is a method. The method includes providing a gas (e.g., metallic gas) into a chamber and ionizing the gas by providing power to a filament to cause the filament to emit electrons in the chamber. Providing power to the filament causes the filament to add heat to the chamber proximate the first end of the chamber. The method also includes reducing or eliminating a temperature gradient in the chamber by operating one or more heaters positioned in the chamber. The one or more heaters are positioned inside the chamber and extend from a second end of the chamber opposite the first end. The method also includes extracting an ion beam from the chamber via an aperture positioned between the filament and the one or more heaters.

In some embodiments, operating the one or more heaters includes causing the one or more heaters to balance the heat added to the chamber by the filament. In some embodiments, the method include measuring temperatures at a plurality of positions in the chamber. Operating the one or more heaters may include controlling the one or more heaters based on the temperatures at the plurality of positions in the chamber. The method may also include measuring a plasma uniformity of the ion beam extracted through the aperture and determining setpoints for the temperatures at the plurality of positions in the chamber based on measurements of the plasma uniformity. The setpoints may be associated with optimal plasma uniformity. The method may also include controlling the one or more heaters to drive the temperatures at the plurality of positions to the setpoints.

In some embodiments, the method includes removing heat from the chamber by operating a water cooling system thermally coupled to the chamber by a plurality of support posts.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, systems and methods relating to a heavy metal ion source are shown, according to various example embodiments, and in particular to use of one or more auxiliary heaters and other heat management features to improve operation of an ion source. Although the primary embodiments shown relate to Bernas ion sources, the teachings herein can also be adapted for Freeman ion sources or other types of ion sources.

Increasing a run-time of the ion source is also an objective of the systems and methods described herein. Some ion sources must be frequently shut off so that a cleaning operation can be executed, for example due to build-up of particles on electrodes or other surfaces in an ion source. However, frequent shutoffs can limit production amounts, create undesirable interruptions, and may be energy inefficient. The systems and methods described are capable of constant operation for relatively long amounts of time, for example by efficiently ionizing metal gas in the ion source and protecting one or more electrodes or other surfaces from condensation in the ion source. In some embodiments, ion sources in accordance with the disclosure herein can be operated constantly for at least several days. As described in detail below, these advantages can be achieved through inclusion and operation of one or more heaters and other temperature-management features.

Another objective of the systems and methods describe herein is to improve consistency of an ion beam (e.g., plasma uniformity) output from the ion source. A highly-consistent ion beam can be associated with highly-efficient production and extraction of a desired ion and minimization of contamination by undesired ions. The systems and methods described herein are capable of providing optimal plasma uniformity. For example, the system and methods described herein can improve plasma uniformity by reducing or eliminating a temperature gradient in the ion source.

For example, some embodiments of the ion sources described herein are configured to produce a beam having a greater than 20 mA (milliampere) singly-charged metallic ion current with high current uniformity. In some embodiments, the ionic mass of the desired isotope is 176 amu (atomic mass units), e.g., $^{176}$Yb.

These and other advantages of the present disclosure are described in detail below with reference to the various figures.

Figure 1:
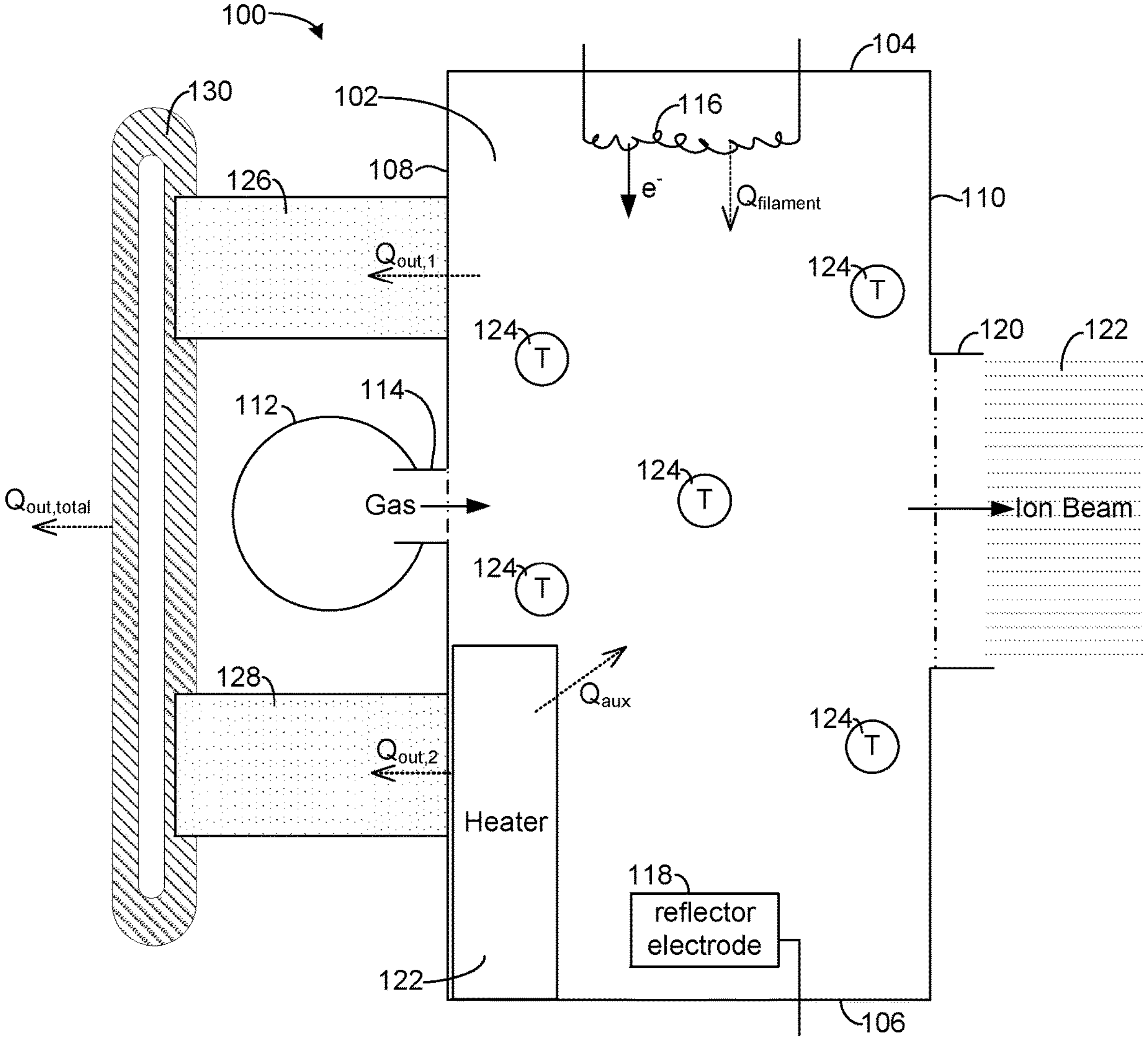
FIG. 1 is a schematic view of an ion source, according to an example embodiment.

Referring now to FIG. 1, a schematic view of an ion source 100 is shown, according to an example embodiment. The ion source 100 is configured for production of an ion beam, for example a heavy metal ion beam, such as a charged Ytterbium isotope beam. For example, the ion source may be configured to output a beam having a greater than 20 mA singly-charged metallic ion current including ions with an ionic mass of 176 amu.

The ion source 100 is shown as including a chamber 102, in which ionization of a metallic gas is performed to produce the ion beam. As shown, the chamber 102 has substantially-rectangular cross-section and includes a first end 104, a second end 106 opposite the first end 104, a first wall 108 extending from the first end 104 to the second end 106, and a second wall 110 opposite the first wall 108. The chamber 102 may be formed as an enclosure by inclusion of a third wall and fourth wall (shown in later figures) positioned to form a six-sided rectangular box.

As shown in FIG. 1, the ion source 100 includes an oven 112 connected to an inlet 114 extending through the first wall 108. The oven 112 is configured to produce and supply a metallic gas into the chamber 102 via the inlet 114 in the first wall 108. For example the oven 112 may supply an Ytterbium gas. In its gaseous state, the metallic gas flows into the chamber 102 and may distribute into the full volume of the chamber 102. The metallic gas may be neutrally-charged when supplied into the chamber 102 by the oven 112. If the metallic gas is allowed to cool and condense, it may build-up on surfaces inside the chamber 102, which may be undesirable for various reasons. For example, deposition of the metallic vapor can short out insulators in the ion source 100. As another example, surfaces coated in the metallic vapor may affect the overall concentration of the gas in the chamber 102 and thus reduce the efficiency of the ion source 100. One aspect of the present disclosure includes approaches for minimizing or eliminating such condensation during operation of the ion source 100.

The ion source 100 is also shown as including a filament 116 positioned at the first end 104 of the chamber 102. The filament 116 is connected to circuitry configured to provide a voltage across the filament 116 which causes the filament 116 to incandesce. While in an incandescent state, the filament 116 emits electrons (shown in FIG. 1 as $e^-$) as well as heat (shown in FIG. 1 as $Q_{filament}$) In some embodiments, when the filament 116 is emitting electrons at a preferred rate for operation of the ion source 100, the filament 116 provides approximately one kilowatt of heat into the chamber 102. The filament 116 may be made of tungsten and may have a diameter of approximately 1.5 millimeters.

The electrons are emitted from the filament 116 inside the chamber 102. Many of the electrons from the filament 116 are emitted into the chamber 102 with a velocity pointing towards the second end 106 (i.e., downward in the perspective of FIG. 1). The ion source 100 is shown to include a reflector electrode 118 positioned at the second end 106 which can reflect electrons back toward the first end 104 (upward in the perspective of FIG. 1). That is, the reflector electrode 118 can be held at a negative voltage so that a repulsive electric force is created between the reflector electrode 118 and the electrons. Operation of the filament 116 and the reflector electrode 118 can thus cause electrons to move about the chamber 102 without collecting at the second end 106.

Electrons and metallic gas are thus both provided into the chamber 102. Interactions between the metallic gas and the electrons cause ionization of the metallic gas. In the example of FIG. 1, the inlet 114 through which gas is provided to the chamber 102 is positioned approximately equidistant from the first end 104 and the second end 106 and approximately equidistant from the filament 116 and the reflector electrode 118. This geometry may facilitate maximally-efficient ionization of the gas provided by the oven 112.

The ionized gas can be extracted from the chamber 102 as an ion beam via aperture 120. The aperture may be an elongated slot or slit, a circular opening, or some other shape in various embodiments. The aperture 120 is shown as being positioned on the second wall 110 opposite the inlet 114. The aperture 120 may be approximately equidistant between the first end 104 and the second end 106, and approximately equidistant between the filament 116 and the reflector electrode 118. In order to extract the ion beam from the chamber, the aperture 120 may be part of an extraction device positioned outside the aperture 120 and configured to pull ionized gas out of the chamber 102 in an ion beam. For example, the extraction device may include a positively-charged electrode which creates an electric field that pulls charged ions through the aperture 120. Various extraction electrode arrangements are possible in various embodiments of the extraction device.

One aspect of the present disclosure is a determination that consistency of the ion beam across a vertical dimension (from the perspective of FIG. 1) of the ion beam depends on consistency of the density of the metallic gas in the chamber 102 over that same direction. For example, an area of higher-density gas would produce more ions which are pulled from the chamber 102 and through the aperture 120 as compared an area of lower-density gas. Because of the charge on those ions, this would create a current gradient in the ion beam which directly corresponds to a density gradient in the metallic gas. Accordingly, one objective of the ion source 100 is to minimize the density gradient of the metallic gas (i.e., to reduce variations in density of the metallic gas within the chamber 102 in order to improve consistency of the ion beam extracted via the aperture 120.

One potential cause of non-uniform density of the metallic gas in the ion source would be variation in temperature across the metallic gas. At higher temperatures, the metallic gas is less dense, whereas the metallic gas is denser at lower temperatures. That is, once ionized, volumes at lower temperature may include more ions for extraction via the aperture 120 as compared to volumes at higher temperature. Accordingly, one aspect of the present disclosure is a recognition that temperature gradients in the chamber 102 can create non-uniformities in the ion beam produced by the ion source 100.

As shown in FIG. 1, the filament 116 produces a first amount of heat while incandescing during operation of the ion source 100. This filament heat is denoted herein as $Q_{filament}$. The filament heat is emitted proximate the first end 104 of the chamber 102 and, accordingly, may tend to create a temperature gradient across the chamber 102 with areas closer to the filament 116 and the first end 104 driven to higher temperatures by the filament heat $Q_{filament}$.

To at least partially balance the filament heat $Q_{filament}$, the ion source 100 includes one or more heaters 122 positioned in the chamber and operable to provide auxiliary heat $Q_{aux}$ into the chamber 102. For example, two heaters 122 may be included. As shown in FIG. 1, the one or more heaters 122 may extend from the second end of the chamber 102 and along the first wall 108. By being positioned proximate the second end of the chamber 102, the one or more heaters 122 are geometrically arranged to oppose the filament 116 without obstructing operation of the reflector electrode 118. The one or more heaters 122 are operable to provide the auxiliary heat $Q_{aux}$ in amounts that at least partially balance the filament heat $Q_{filament}$ so as to reduce or eliminate a temperature gradient in the chamber 102 which may otherwise be caused by the filament heat. For example, in some embodiments or in some scenarios, the one or more heaters 122 are controlled such that $Q_{aux}=Q_{filament}$. Various control strategies for the one or more heaters 122 are described in detail below.

Operation of the one or more heaters 122 can also reduce or eliminate formation of condensation on the reflector electrode 118 (e.g., on an insulator of the reflector electrode 118) or other surfaces in the ion source 100. When the metallic gas is above a certain temperature, the metallic gas remains gaseous and moves about the chamber 102. However, below a certain temperature, the metallic gas may condense and collect on surfaces of the ion source 100. Build-up of the condensate on the reflector electrode 118 can prevent the reflector electrode 118 from operating as intended. For example, when coated with a condensed film, the reflector electrode 118 may no longer be electrically isolated from the plasma. The one or more heaters 122 provide heat proximate the reflector electrode 118 which keeps the temperature of the metallic gas (and of the reflector electrode 118 itself) high enough to prevent build-ing of metallic condensate on the reflector electrode 118. Build-up of condensate on other surfaces (e.g., on the heater 122) is prevented as well. Operation of the one or more heaters 122 during ion production can thus extend the operation lifetime of the ion source 100 and allow the ion source 100 to be operated for a relatively long time (e.g., several days) without the need for intermittent cleaning as required by other designs.

As shown in FIG. 1, the ion source 100 includes multiple temperature sensors (e.g., thermocouples) 124 placed at multiple positions in the ion source. In the example shown, five thermocouples 124 included at various positions in the ion source. Other numbers of thermocouples 124 can be included in various embodiments. By measuring the temperature at multiple positions in the chamber 102, temperature differences and gradients across the ion source 100 can be measured. For example, a temperature sensor 124 proximate the filament 116 may measure a higher temperature than a temperature sensor 124 positioned proximate the one or more heaters 122, which may indicate that operation of the one or more heaters 122 should be adjusted to better balance $Q_{filament}$ and reduce or eliminate a temperature gradient in the ion source 100. The temperature sensors 124 may be arranged in the chamber 102 to obtain representative measurements of temperatures throughout the chamber 102. Multiple temperatures can thus be monitored in real-time to facilitate control of the one or more heaters 122 as described in detail below with reference to FIGS. 2-3.

The ion source 100 also facilitates temperature management in the chamber 102 by including thermally-conductive support posts, shown in FIG. 1 as a first post 126 and a second post 128. Other numbers of thermally-conductive support posts are included in various embodiments (e.g., four as shown in FIGS. 5-8), with the schematic view of FIG. 1 showing the first post 126 and the second post 128 for the sake of illustration. The thermally-conductive support posts (e.g., first post 126 and the second post 128) are configured to physically support the chamber 102 (e.g., hold the chamber 102 in a desired position) and to provide for heat flow out of the chamber 102 as described in the following passages.

As an initial matter, the ion source 100 is preferably positioned in a vacuum, for example at a pressure of approximately $6\times10^{-7}$ torr, with the chamber 102 at between $2\text{-}3\times10^{-5}$ during operation. Accordingly, the primary pathway for heat to leave the chamber 102 is through any physical structures in contact with the chamber. The ion source 100 is thus designed for ideal heat flow away from the chamber 102 via the support posts 126, 128.

During operation of the ion source 100, the filament 116 provides a large amount of heat $Q_{filament}$ into the chamber 102, for example on the order of approximately one kilowatt. The heater 122 provides auxiliary heat $Q_{aux}$ to balance $Q_{filament}$ and is of a similar order of magnitude as $Q_{filament}$ (e.g., also on the order of approximately one kilowatt). Accordingly, in order for temperatures in the chamber 102 to be maintained at substantially constant temperatures (e.g., to prevent the chamber 102 form over-heating), an amount of heat approximately equal to $Q_{aux}+Q_{filament}$ is removed from the ion source 100 via the thermally-conductive support posts 126, 128.

The thermally-conductive support posts 126, 128 are preferably made of a material with a high thermal-conductivity and good electrical conductivity. For example, the thermally-conductive support posts 126, 128 may be made of molybdenum. The chamber 102 may be electrically grounded via the support posts 126, 128. As shown, the first post 126 provides for heat $Q_{out,1}$ to flow out of the chamber 102 via the first post 126, while the second post 128 provides for heat $Q_{out,2}$ to flow out of the chamber 102 via the second post 128. In the embodiment shown (e.g., with two posts), the thermal dynamics of the ion source 100 are preferably such that $|Q_{out,1}+Q_{out,2}|\approx|Q_{aux}+Q_{filament}|$. In other embodiments where N thermally-conductive posts are provides, the thermal dynamics of the ion source 100 are preferably such that $|Q_{out,1}+Q_{out,2}+\ldots+Q_{out,N}|\approx|Q_{aux}+Q_{filament}|$.

The thermally-conductive supports posts 126, 128 extend from the first wall 108 of the chamber 102 to a cooling system, for example a water-cooling system 130 as shown. Because the thermally-conductive support posts 126, 128 are at different positions on the first wall 108, the heat flows $Q_{out,1}$ and $Q_{out,2}$ may be somewhat unequal. For example, the second post 128 is positioned proximate the one or more heaters 122 which may cause a value of $Q_{out,2}$ to be greater than $Q_{out,1}$. However, the support posts 126, 128 are positioned generally symmetrically relative to the chamber 102 and are thereby arranged to avoid creating unwanted imbalances or temperature variations in the chamber 102 as heat flows out of the chamber 102 via the support posts 126, 128.

The water-cooling system 130 is configured to circulate water (or another fluid or refrigerant) across the thermally-conductive support posts 126, 128 to remove heat from the posts 126, 128. The posts 126, 128 may be in direct contact with the fluid or may transfer heat to the fluid via one or more intermediary structures. The water-cooling system 130 is configured to dissipate the heat from the ion source 100 into the ambient environment. In some embodiments, the water-cooling system 130 includes a chiller or other refrigeration system for removing heat from the fluid so that chilled water (i.e., colder than ambient) is circulated to the support posts 126, 128, absorbs heat from the support posts 126, 128, and returns to the chiller or other refrigeration system to be rechilled. In other embodiments, the water-cooling system 130 includes a heat exchanger (e.g., coil) and, optionally, a fan to facilitate heat transfer from the fluid to an ambient environment without use of a chiller or refrigeration system.

The water-cooling system 130 can be configured for calorimetry measurements, i.e., to measure the amount of heat extracted by the water-cooling. For example, the water-cooling system 130 may measure a supply water temperature and a return water temperature and use those measurements in combination with data indicative of a flow rate to calculate an amount of heat removed by the water-cooling system 130, shown in FIG. 1 as $Q_{out,total}$. The values of $Q_{out,total}$ may preferably be approximately equal to $Q_{aux}+Q_{filament}$ and are used in some embodiments to estimate $Q_{aux}$ and $Q_{filament}$. In some embodiments, the water-cooling system 130 is controlled using a feedback loop based on a setpoint for $Q_{out,total}$. In some embodiments, the water-cooling system 130 is controlled based at least in part on measurements from the temperature sensors 124 in the chamber 102.

The ion source 100 thus includes various elements which facilitate temperature and heat management at the ion source 100 in order to maximize the operating time of the ion source 100 while also optimizing consistency of the ion beam extracted from the chamber 102.

Figure 2:
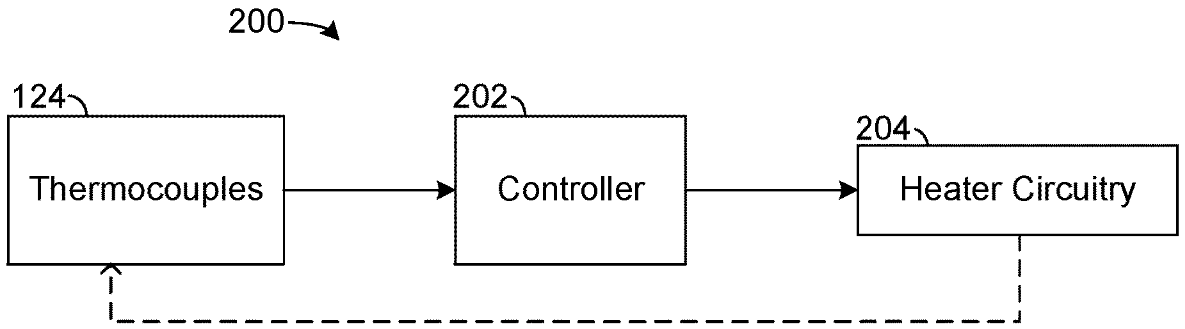
FIG. 2 is a block diagram of a control loop for the ion source of FIG. 1, according to an example embodiment.

Referring now to FIG. 2, a block diagram of a control loop 200 for the one or more heaters 122 of the ion source 100 is shown, according to an example embodiment. The control loop 200 is shown as including thermocouples 124, a controller 202, and heater circuitry 204. The heater circuitry 204 may include one or more power supplies or other electronics elements which are controllable to affect operation of the one or more heaters 122 of FIG. 1, in particular to vary a power (heat) output of the one or more heaters 122. Where multiple heaters 122 are included, the heater circuitry 204 may be configured such that the multiple heaters 122 can be independently controlled.

As shown in FIG. 2, the controller 202 is configured to provide an input (e.g., control signal) to the heater circuitry 204, which causes the heater circuitry 204 to operate to affect temperature measurements collected by the thermocouples 124 (i.e., via operation of the heaters 122). The thermocouples 124 provide that output of the physical system (i.e., the temperature measurements) back to the controller 202. The measurements, control signals, etc. can be analog or digital in various embodiments. In the illustration of FIG. 2, the solid lines represent communications between elements and the dotted line indicates thermal dynamics which creates the control loop 200.

In some embodiments, the controller 202 generates control inputs for the heater circuitry 204 based on one or more setpoints for the thermocouples 124. For example, the controller 202 may use feedback control logic (e.g., proportional-integral control, proportional-integral derivative control) to generate control inputs which are configured to drive the measurements from the thermocouples 124 all towards one shared temperature setpoint. The controller 202 can thus operate to minimize temperature gradients in the chamber 102. As another example, the controller 202 may use feedback control logic adapted to generated control inputs which are configured to drive measurements from each thermocouple 124 toward a thermocouple-specific setpoint for each thermocouple 124. In some embodiments, the setpoints are learned based on a measured property of the ion beam (e.g., plasma uniformity), for example as described in detail below with reference to FIG. 10. The controller 202 can thus operate to optimize a property of the ion beam, for example plasma uniformity.

In other embodiments, the controller 202 is configured to generate control inputs for the heater circuitry 204 which are adapted to drive differences between the temperature setpoints toward zero. For example, the controller 202 may be configured to generate control inputs that minimize an error function which compares the measurements from the multiple thermocouples 124 (e.g., using an extremum-seeking control approach). In such a case, the controller 202 is adapted to cause the one or more heaters 122 to reduce or eliminate a temperature gradient in the chamber 102 without use of predetermined temperature setpoints. Various control approaches are possible in various embodiments.

In some embodiments, dynamic control of the heater circuitry 204 to vary the heat output by the heaters 122 is sufficient to provide a desired reduction or elimination of a temperature gradient in the chamber 102 and to provide the benefits associated therewith described herein. In such embodiments the control loop 200 and the controller 202 need not communicate with other elements of the ion source 100 and can be provided in isolation as illustrated in FIG. 2. In other embodiments, for example as shown in FIG. 3 and described in detail with reference thereto, a comprehensive, unified control system can be provided in some embodiments.

Figure 3:
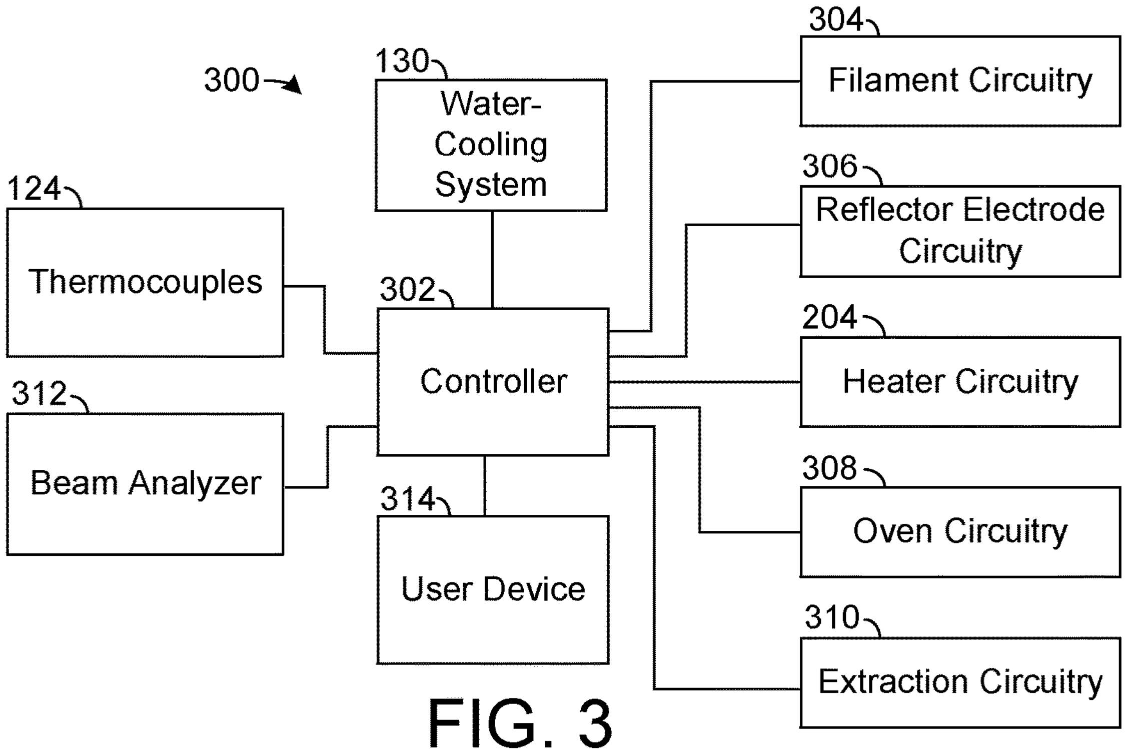
FIG. 3 is block diagram of a control system for the ion source of FIG. 1, according to an example embodiment.

Referring now to FIG. 3, a control system 300 for use with the ion source 100 is shown, according to an example embodiment. In some embodiments, the control loop 200 is executed using the control system 300. The control system 300 is shown as including a controller 302, the thermocouples 124, the water-cooling system 130, the heater circuitry 204, filament circuitry 304, reflector electrode circuitry 306, oven circuitry 308, extraction circuitry 310, a beam analyzer 312, and a user device 314. Various other embodiments of the control system 300 can include any combination of these elements.

The filament circuitry 304 includes electronics components configured to control the amount of power provided to the filament 116. The reflector electrode circuitry 306 includes electronics components configured to affect the electric field provided by the reflector electrode 118. The oven circuitry 308 includes electronics components configured to affect operation of the oven 112, for example to affect a temperature of the gas provided into the chamber 102 and/or an amount of the gas provided into the chamber 102. The extraction circuitry 310 is configured to provide and, in some embodiments, controllably modify an electric field at the aperture 120 which is configured to extract the ion beam from the chamber 102 via the aperture 120.

The beam analyzer 312 is configured to analyze one or more properties of the ion beam produced by the ion source 100, i.e., extracted via the aperture 120. For example the beam analyzer 312 may be configured to measure a plasma uniformity of the ion beam. The beam analyzer 312 may be useable during online ion production by the ion source, or may be used during setup (testing, calibration, etc.) of the ion source 100.

The user device 314 is configured to allow a user to interact with the controller 302, for example to adjust settings of the controller 302, provide a command to the controller 302, etc. The user device 314 may also be configured to display information to the user relating to operation of the ion source 100.

In the embodiment of FIG. 3, the controller 302 is communicable with the thermocouples 124, the beam analyzer 312, the filament circuitry 304, the reflector electrode circuitry 306, the heater circuitry 204, the oven circuitry 308, the extraction circuitry 310, the water cooling system 130, and the user device 314. The controller 302 is configured to coordinate control of the water-cooling system 130, the filament circuitry 304, the reflector electrode circuitry 306, the heater circuitry 204, the oven circuitry 308, and/or the extraction circuitry 310, for example based on inputs from the thermocouples 124, from the beam analyzer 312, and/or from other elements of the control system 300. The controller 302 may be primarily configured for temperature and heat management for the ion source 100, but may also provide various control functionality relating to other aspects of operation of the ion source 100, for example ionization and extraction.

As one example of coordinated control that can be provided by the controller 302 in various embodiments, the controller 302 may control the water-cooling system 130 in coordination with control of the heater circuitry 204, for example to cause the water-cooling system 130 to vary amount of cooling provided to the support posts 126, 128 proportionally to changes in the amount of heat provided by the one or more heaters 122. Control of the water-cooling system 130 and the one or more heaters 122 can thus be coordinated or unified to help manage temperatures of the ion source 100.

As another example of coordinated control that can be provided by the controller 302, the controller 302 may receive a signal from the filament circuitry 304 indicative of a power consumption of the filament 116. The controller 302 may use that information to generate a control signal for the heater circuitry 204, for example so that the one or more heaters 122 can be controlled to operate at the same or similar power level as the filament 116 (e.g., to produce a same amount of heat). The controller 302 may communicate with the oven circuitry 308 to account for heat provided to the chamber 102 by the oven when controlling the heater circuitry 204 or other aspects of the control system 300.

As another example of control enabled by the control system 300 of FIG. 3, the controller 302 may be enabled to use measurements from the beam analyzer 312 in feedback control of one or more of the water-cooling system 130, the filament circuitry 304, the reflector electrode circuitry 306, the heater circuitry 204, the oven circuitry 308, and/or the extraction circuitry 310. For example, the heater circuitry 204 may controlled by the controller 302 in a feedback loop that seeks to optimize a parameter measured by the beam analyzer 312, for example a plasma uniformity. As another example, the beam analyzer 312 can be used in a setup (e.g., training, configuration, calibration) stage to train the controller 302 (e.g., to determine values, weights, etc. of an algorithm used by the controller 302) so that the controller 302 can control one or more of the water-cooling system 130, the filament circuitry 304, the reflector electrode circuitry 306, the heater circuitry 204, the oven circuitry 308, and/or the extraction circuitry 310 to optimize the plasma uniformity (or other parameter) of the ion beam.

The control system 300 can enable various such control modalities in various embodiments.

Figure 4:
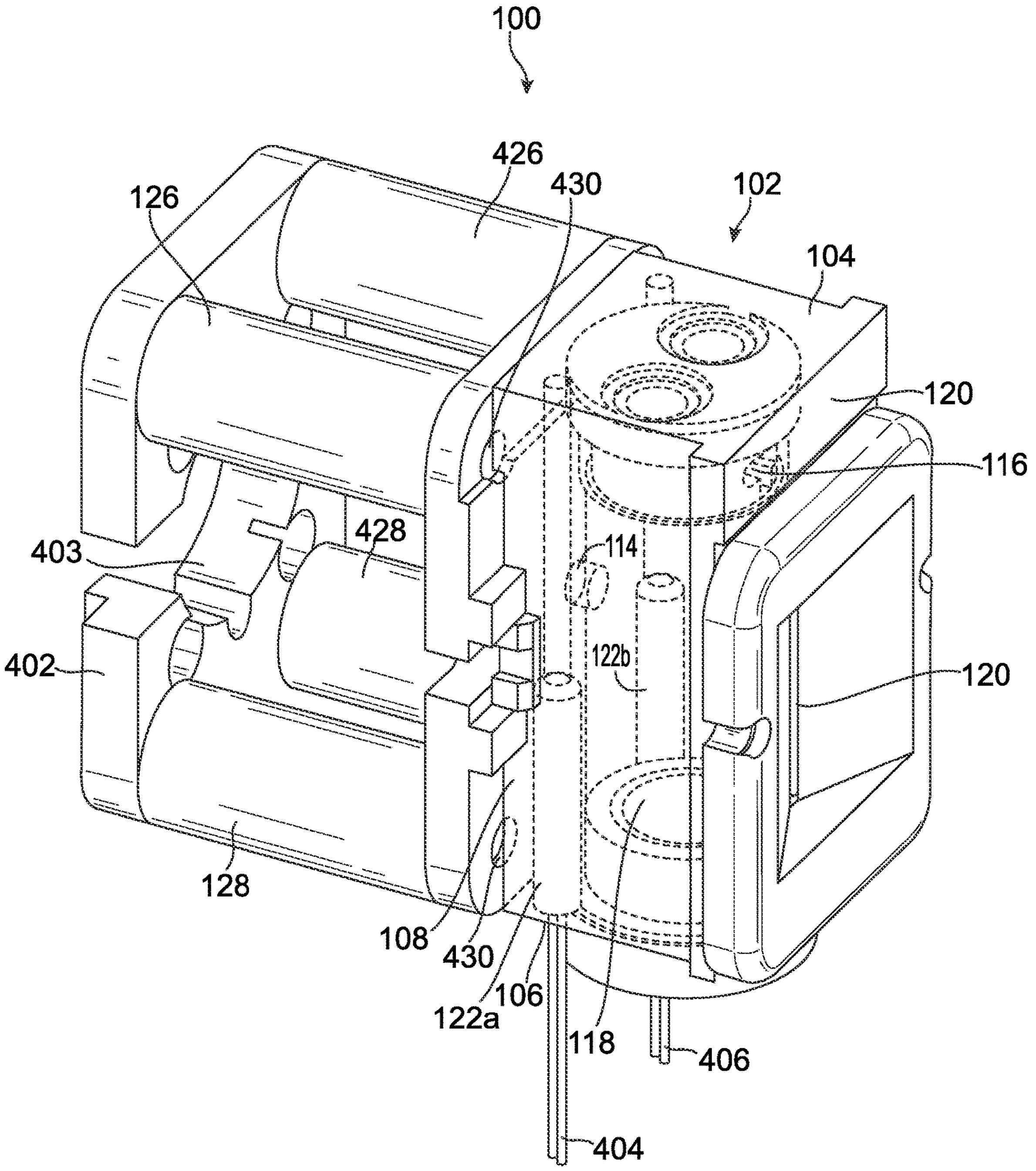
FIG. 4 is a perspective view of the ion source of FIG. 1, according to an example embodiment.
Figure 5A:
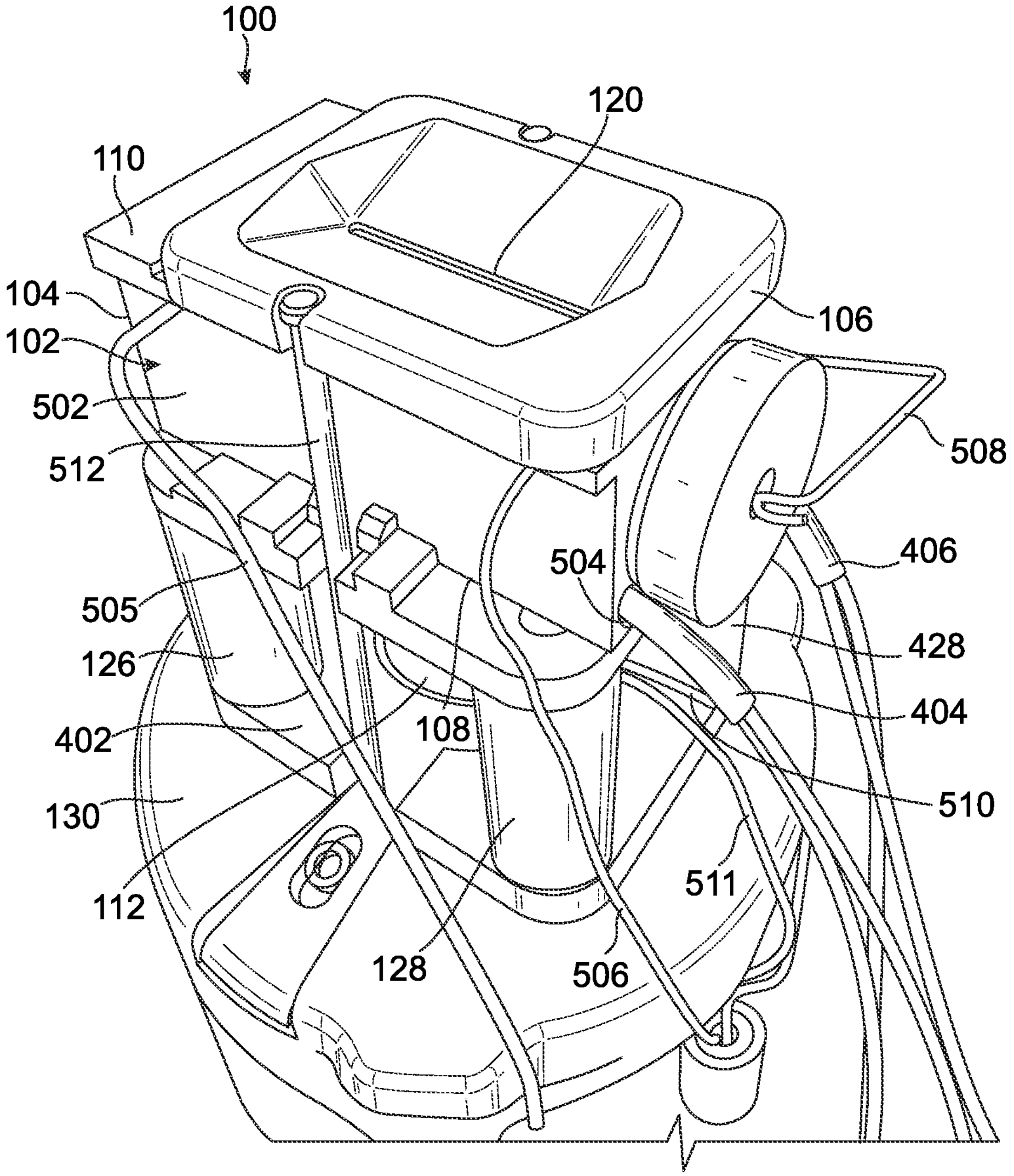
FIG. 5A is another perspective view of the ion source of FIG. 1, according to an example embodiment.
Figure 5B:
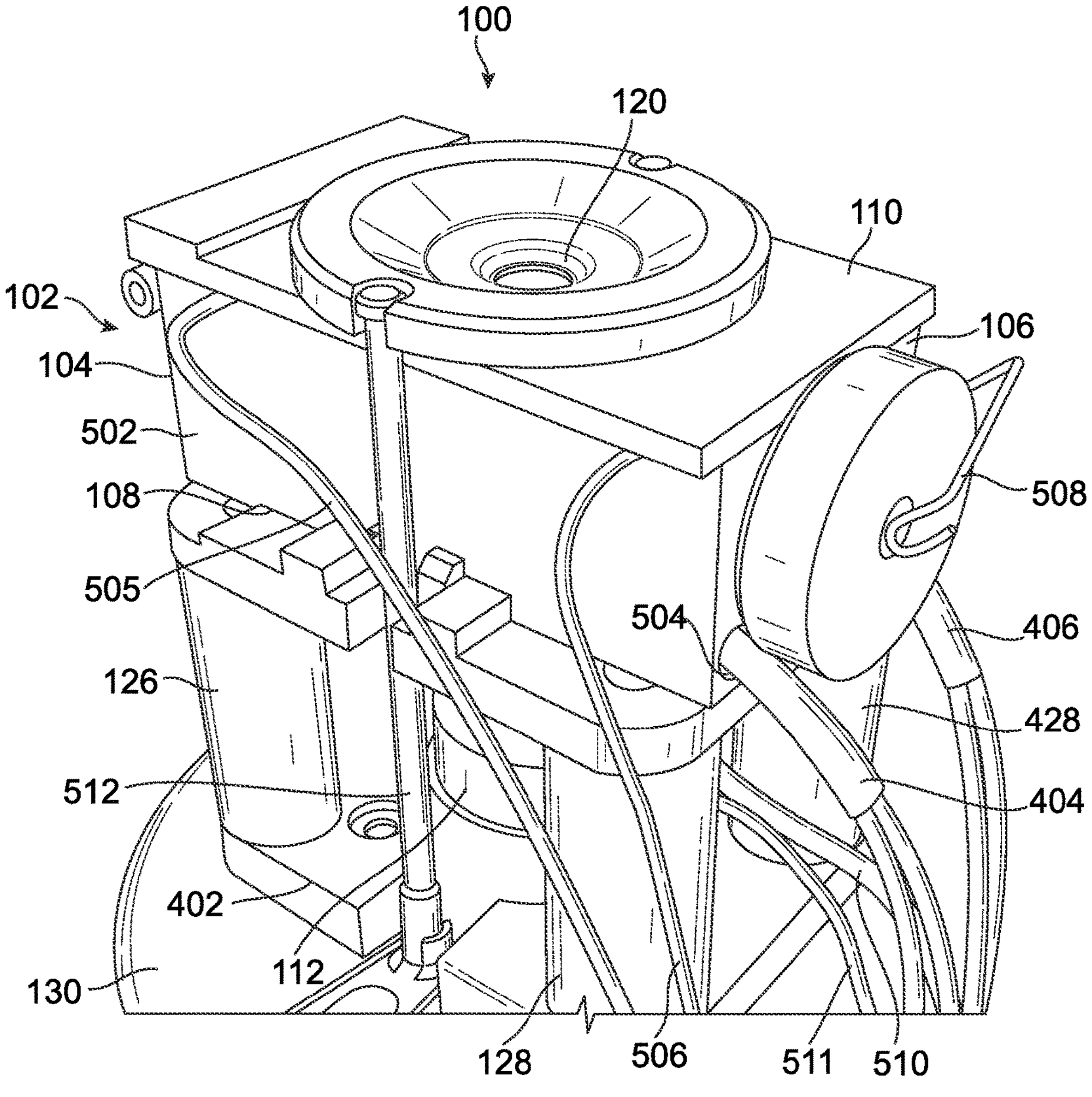
FIG. 5B is a perspective view of an ion source, according to an example embodiment.
Figure 6:
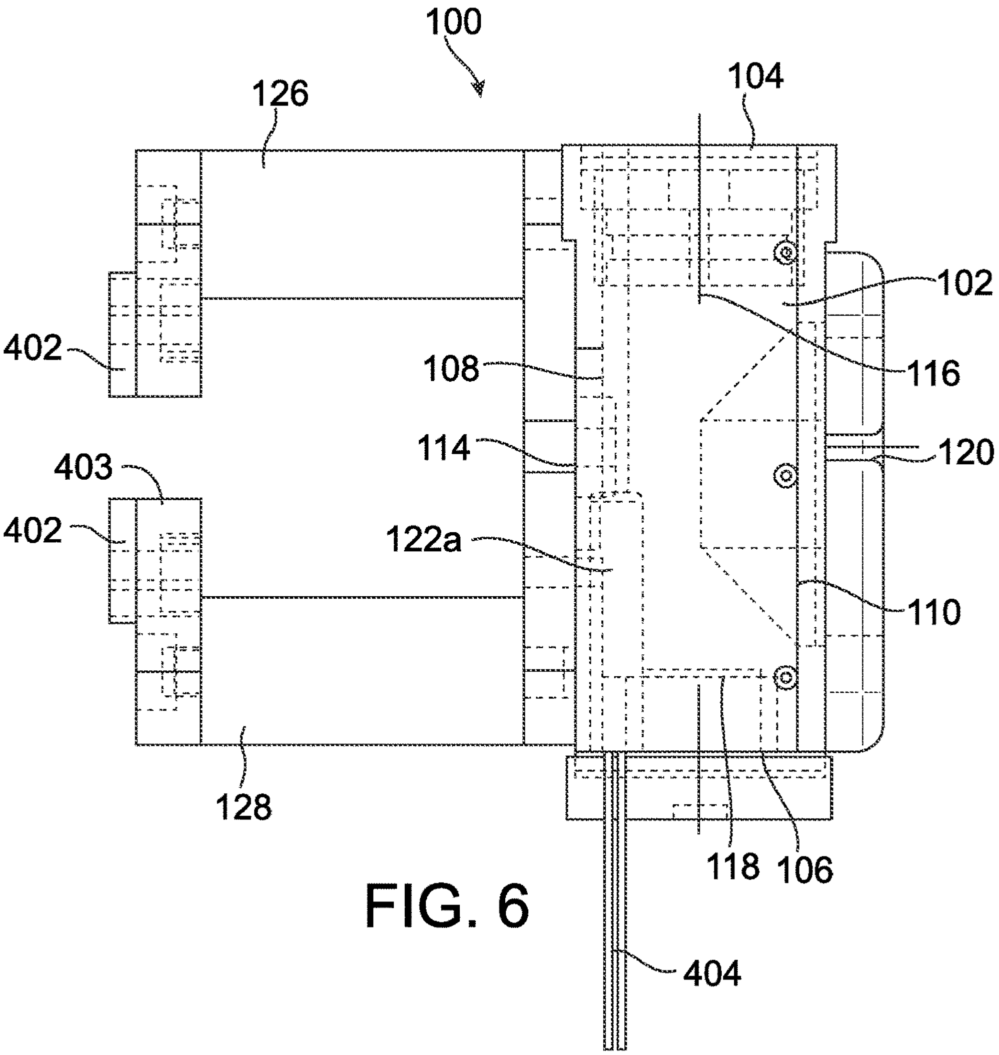
FIG. 6 is a first cross-sectional view of the ion source of FIG. 4, according to an example embodiment.
Figure 7:
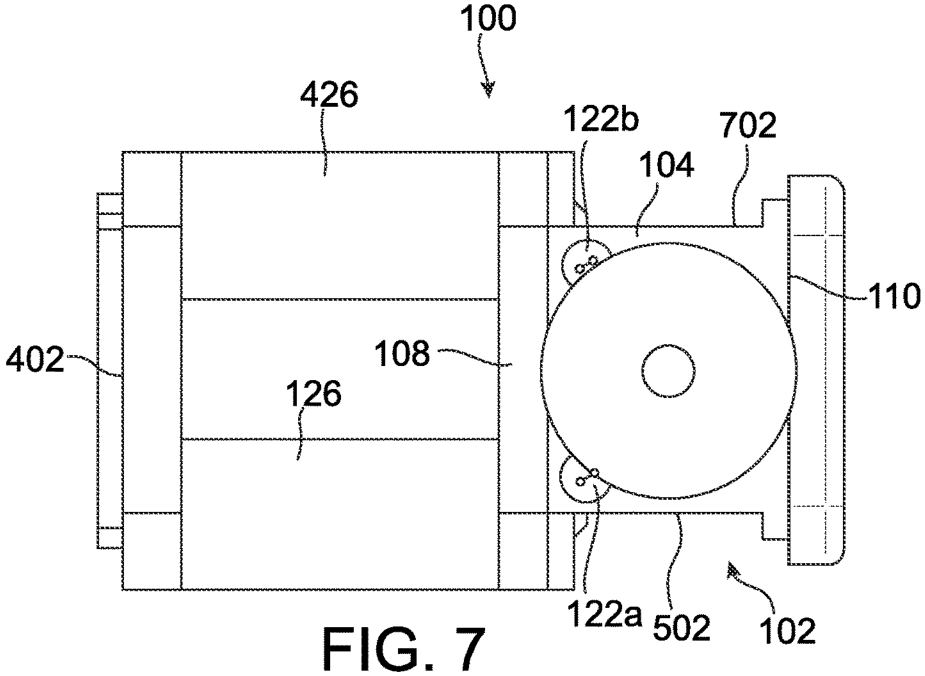
FIG. 7 is a second cross-sectional view of the ion source of FIG. 4, according to an example embodiment.
Figure 8:
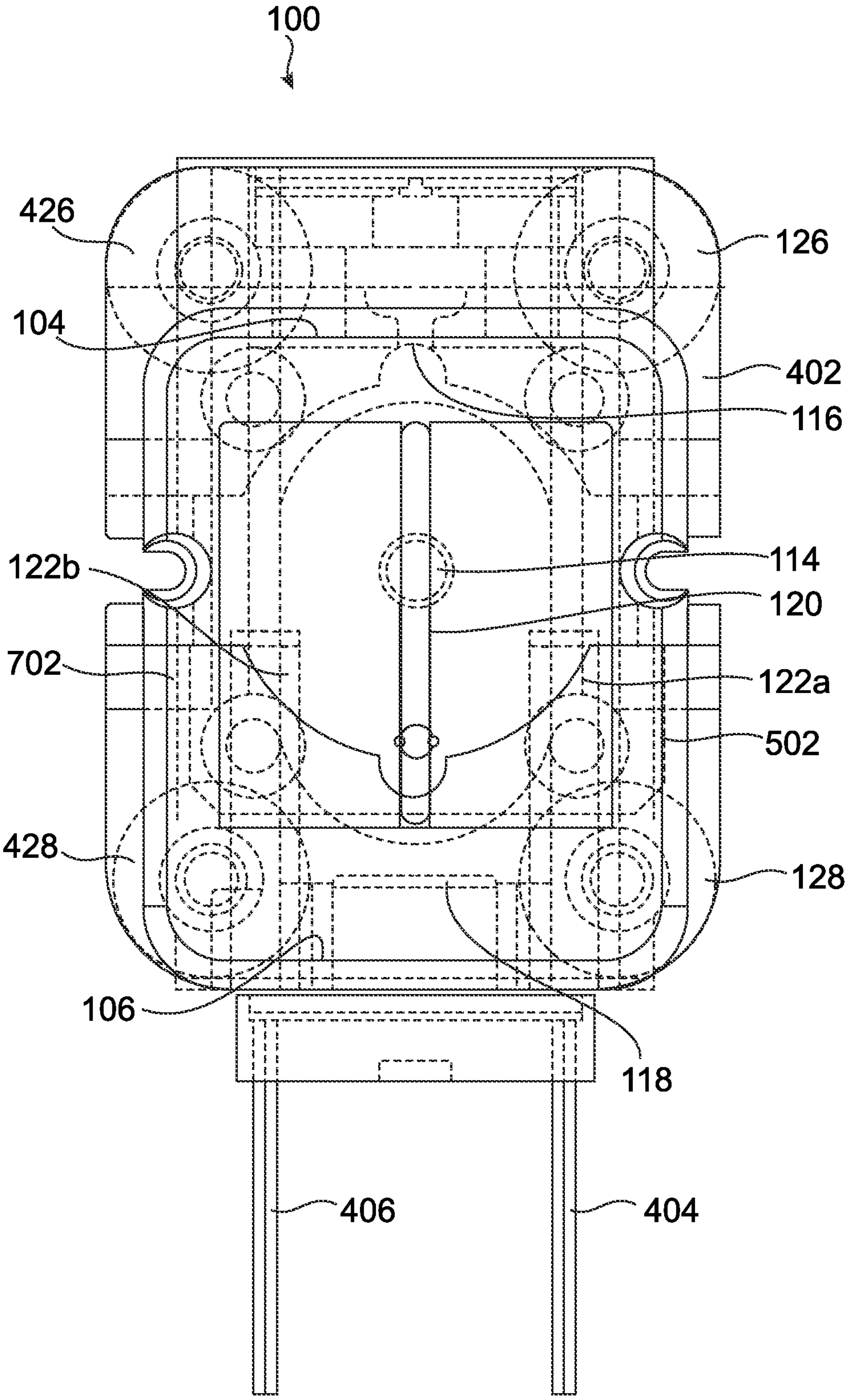
FIG. 8 is a third cross-sectional view of the ion source of FIG. 4, according to an example embodiment.

Referring now to FIGS. 4-8, various depictions of example embodiments of the ion source 100 are shown. In particular, FIG. 4 shows a cut-away perspective view of the ion source 100, FIG. 5A shows a perspective view of an exterior of the ion source 100, FIG. 5B shows a perspective view of an exterior of the ion source 100 in an alternative embodiment, and FIGS. 6-8 show drawings of the ion source 100 from three orthogonal perspectives.

FIGS. 4-8 show the chamber 102 defined by the first end 104, the second end 106 opposite the first end 104, a first wall 108 extending from the first end 104 to the second end 106, and a second wall 110 opposite the first wall, as described above with reference to FIG. 1. In FIGS. 5A-B, a third wall 502 is visible and connects with the first end 104, the second end 106, and the first wall 108, and the second wall 110. A fourth wall 702 of the chamber 102 is visible in FIGS. 7 and 8, is positioned opposite the third wall 502, and also connects with the first end 104, the second end 106, the first wall 108, and the second wall 110. The chamber 102 is thus formed as a six-sided rectangular box in the example shown. Other shapes are possible in other embodiments.

FIGS. 4-9 also show a third post 426 and a fourth post 428 extending from first wall 108 of the chamber 102. The third post 426 and the fourth post 428 are configured substantially the same as the first post 126 and the second post 128 described above. For example, the first post 126, second post 128, third post 426, and fourth post 428 may have approximately equal dimensions and provide approximately equivalent pathways for heat transfer (e.g., differing by less than manufacturing tolerances). Like the first post 126, the third post 426 is positioned proximate the first end 104 of the chamber 102 and the filament 116. Like the second post 128, the fourth post 428 is positioned proximate the second end 106 of the chamber 102 and the heaters 122.

The first post 126, second post 128, third post 426, and fourth post 428 are shown in FIGS. 4-9 as extending from the first wall 108 of the chamber 102 to a plate 402. The plate may be thermally-conductive such that heat can flow from the posts 126, 128, 426, 428 into the plate 402. The plate 402 may then be in thermal contact with water-cooling system 130 in order for heat to be dissipated to the water-cooling system 130 as described with reference to FIG. 1. In some embodiments, the first post 126, second post 128, third post 426, and fourth post 428 can be in direct thermal contact with the interior of the chamber 102 via channels 430 through the first wall 108 as shown in FIG. 4.

The plate 402 has a central opening 403 through which the oven 112 can extend, for example as shown in FIGS. 5A-B. This allows the oven 112 to be positioned primarily on an opposite side of the plate 402 relative to the chamber 102 while routing the metallic gas from the oven 112 to the chamber 102. This arrangement enables the oven 112 to be significantly larger than shown in the schematic illustration of FIG. 1.

As shown in FIGS. 4-8, the ion source includes two heaters 122, shown as a first heater 122*a* and a second heater 122*b*. The heaters 122*a,b* are shown as being cylindrical and extending from corners of the chamber 102. In particular, the first heater 122*a* extends from the second end 106 and along an edge between the first wall 108 and the third wall 502 while the second heater 122*b* extends from the second end 106 along an edge between the first wall 108 and the fourth wall 702. The height of the heaters 122*a,b* may be selected so that the heaters 122*a,b* end just below the inlet 114 for the gas from the oven 112. The heaters 122*a,b* are shown as being symmetrical across a centerline of the ion source. In some embodiments, the ion source is substantially symmetrical across the centerline. In some embodiments, the first heater 122*a* and the second heater 122*b* are metal-ceramic resistive heaters.

FIGS. 4-8 show first heater leads 404 extending from the first heater 122*a* and second heater leads 406 extending from the second heater 122*b*. The first heater leads 404 provide for transmission of electrical power to the first heater 122*a* (which the first heater 122*a* uses to generate heat), while the second heater leads 406 provide for transmission of electrical power to the second heater 122*b* (which the second heater 122*b* uses to generate heat). The first heater leads 404 and the second heater leads 406 may connected to and/or included with the heater circuitry 204 shown in FIGS. 2-3, which may include electronics components configured to provide variable and controllable amounts of power to first heater 122*a* and the second heater 122*b*. The first heater leads 404 and the second heater leads 406 are shown as extending through passages 504 formed through the second end 106 of the chamber 102. A gasket or other sealing structure can be provided at the passages 504 in some embodiments.

FIGS. 4-8 also show a first wiring conduit 505 and a second wiring conduit 506 extending into the chamber 102 via an end between the second wall 110 and the third wall 502. The first wiring conduit 505 and the second wiring conduit 506 are connected to temperature sensors (e.g., thermocouples) 124 positioned inside the chamber 102 and are configured to provide communication of measurements collected by the temperature sensors 124 out of the chamber 102. In some embodiments, each wiring conduit 505, 506 is connected to one temperature sensor 124. In other embodiments, each wiring conduit 505, 506 is connected to multiple temperature sensors 124 such that the first wiring conduit 505 and the second wiring conduit 506 combine to provide for communication of readings of four or more temperature sensors 124 out of the chamber 102 (e.g., five temperature sensors 124 as in FIG. 1). The first wiring conduit 505 and the second wiring conduit 506 can be connected to the controller 202 of FIG. 2 or the controller 302 of FIG. 3 in various embodiments.

Also shown in FIGS. 5A-B is a reflector electrode lead 508. The reflector electrode lead 508 is positioned on an exterior of the chamber 102 to provide easy access for a technician to manipulate the reflector electrode lead 508. As shown in FIGS. 5A-B, one end of the reflector electrode lead 508 is in electrical contact with the reflector electrode 118. The reflector electrode lead 508 may also be connected to the filament 116 so as to put the reflector electrode 118 at an electrical potential corresponding to that of the filament 116. For example, the reflector electrode lead 508 may be at approximately −100V. The reflector electrode 118 can thereby be configured to repel electrons as described above with reference to FIG. 1. The reflector electrode lead 508 can also be manually disconnected from the reflector electrode 118 so that the reflector electrode 118 is not connected to an electrical current external to the chamber 102 and is floating. This arrangement may be desirable in some scenarios for use of the ion source 100.

FIGS. 5A-B also show an oven lead 511 configured to connect an element of the oven 112 to control circuitry. For example, the oven lead 511 may be used to control a valve that can control the amount of metallic gas provided to the chamber 102. FIGS. 5A-B also show a gas line 510 which is connected to the chamber 102 proximate the oven 112 and can provide an auxiliary gas (e.g., xenon) to the chamber 102 either during operation of the ion source 100 to produce an ion beam or during a cleaning or other off-line state of the ion source 100.

FIGS. 5A-B also show a bolt 512 which configured to hold the various components described herein together in an assembly. In particular, FIGS. 5A-B show the bolt 512 as engaging the chamber proximate the aperture 120 and engaging the water cooling system 130 and/or the oven 112 proximate the plate 402.

With regards to the aperture 120, FIGS. 4, 5A, and 6-8 show the aperture 120 as an elongated slot aligned with a centerline of the chamber 102. In such embodiments, the aperture 120 has a length along the longitudinal direction of the second wall 110. In such embodiments, the width of the aperture 120 is significantly less than the length. For example, the aperture 120 may be formed as a slot having a width of less than one centimeter and a length of approximately 4 centimeters. FIG. 5B shows an alternative embodiment where the aperture 120 is circular, for example having a radius of approximately one centimeter. Various designs of the aperture 120 are possible in various applications, for example depending on configuration of down-stream processing stages for the ion beam produced by the ion source 100. For example, the elongated slot embodiment of FIG. 5A may be preferable for the primary applications described herein. In some embodiments, different apertures 120 are interchangeable to allow the ion source 100 to be selectively compatible with different down-stream processing stages for the ion beam produced by the ion source 100, for example by removing and replacing an aperture emission plate at the second wall 110 of the chamber 102.

Figure 9:
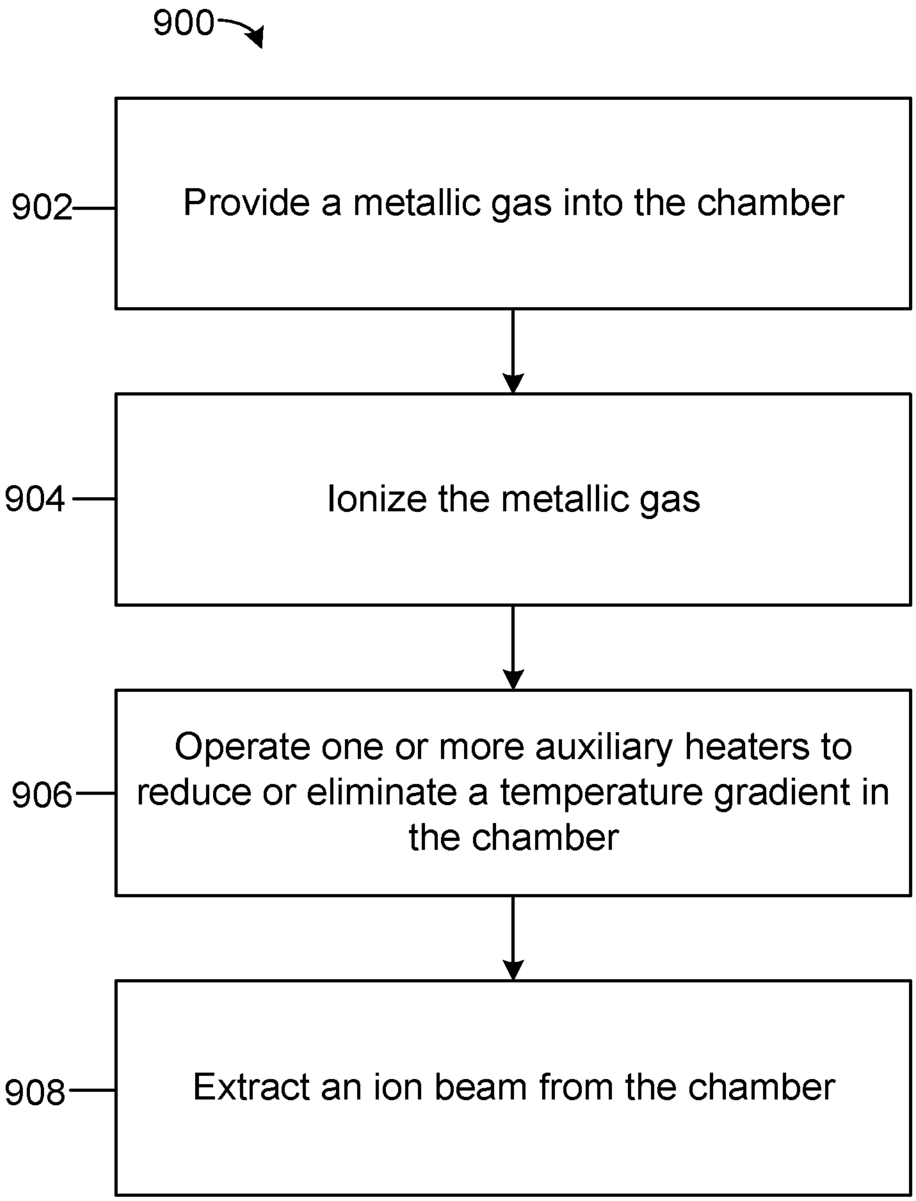
FIG. 9 is a flowchart of a process of operating an ion source, according to an example embodiment.

Referring now to FIG. 9, a flowchart of a process 900 for operating an ion source is shown according to an example embodiment. The process 900 can be performed using the ion source 100, for example, and reference is made thereto in the following description. However, the process 900 may be executable with other ion sources in various embodiments. Similarly, in some embodiments, the process 900 is performed at least in part by operation of the control loop 200 and/or the control system 300 of FIGS. 2-3.

At step 902, a metallic gas is provided into the chamber. The metallic gas may be an Ytterbium gas, for example. In the example of the ion source 100 described above, step 902 includes operating the oven 112 to provide the metallic gas into the chamber via the inlet 114. Step 902 can include controlling the amount of the metallic gas provided into the chamber, for example such that a desired flowrate of metallic gas is provided into the chamber.

At step 904, the metallic gas is ionized. In the example of the ion source 100, the filament 116 is operated to emit electrons which interact with the metallic gas to ionize the metallic gas. As a result of step 904, heavy metal ions are held in the chamber 102, for example mixed with not-yet-ionized gas.

At step 906, one or more auxiliary heaters are operated to reduce or eliminate a temperature gradient in the chamber, i.e., a difference or range of temperatures across multiple points in the chamber. Step 906 can include controlling one or heaters 122 to provide auxiliary heat in the chamber 102 as described in detail above. In some embodiments, step 906 is focused on reducing or eliminating a temperature gradient across the entire chamber. In other embodiments, step 906 is focused on reducing or eliminating a temperature gradient within a sub-volume of the chamber, for example a region proximate an aperture of the chamber through which an ion beam extracted in step 908.

In some embodiments, step 906 includes collecting temperature measurements from multiple points in the chamber and controlling one or more auxiliary heaters based on the measurements. For example, the auxiliary heaters can be controlled to drive the temperature measurements to a shared common setpoint to substantially eliminate or attempt to eliminate a temperature gradient in the chamber. As another example, the auxiliary heaters can be controlled to drive the temperature measurements from different points in the chamber to multiple different setpoints, which may correspond to a reduced temperature gradient in the chamber and can be determined through a learning or optimization process. As another example, the auxiliary heaters can be controlled using control logic configured to minimize an error function that characterizes differences between the multiple temperature measurements. In yet another example, step 906 includes operating the auxiliary heaters at a predetermined power level which is selected to balance heat generated by an incandescing filament during normal operation of the ion source.

Accordingly, as a result of step 906, the chamber may be substantially isothermal, i.e., having approximately the same temperature throughout the chamber, or may be closer to an isothermal state than in a scenario where the auxiliary heaters are not operated in step 906. Because of physical relationship between temperature and density of the metallic gas, step 906 can also be characterized as operating one or more auxiliary heaters to reduce or eliminate a density gradient (i.e., differences in density) of the ionized metallic gas in the chamber. Step 906 and operation of the auxiliary heaters can thereby provide the ionized gas with a substantially uniform density, at least in a region proximate an aperture of the ion chamber.

At step 908, an ion beam is extracted from the ion chamber. The ion beam can be extracted by providing an electrical field at an aperture of the chamber which pulls the charged heavy metal ions out of the chamber via the aperture. Because the density of the ions is substantially uniform proximate the aperture due to successful execution of step 908, the ion beam may be provided with a high degree of uniformity. For example, any currents in a transverse direction of the ion beam may be minimized. The ion beam extracted from the ion chamber may have an optimized plasma uniformity. Accordingly, the ion beam extracted from the ion chamber may be well-suited for various purposes in different embodiments, for example efficient and effective processing in down-stream processing steps for the ion beam. As one example, the ion beam may be well-suited for efficient and accurate filtering of a desired isotope from the ion beam, for example Ytterbium-176.

Steps 902, 904, 906, and 908, shown as a sequence in FIG. 9, can be executed simultaneously to provide for continuous production of a highly-uniform ion beam. In this regard, operation of the auxiliary heaters in step 906 may have an additional benefit of reducing or preventing undesirable condensation of the metallic gas on surfaces in the ion source, for example on a reflector electrode. Execution of step 906 simultaneously with steps 902, 904, and 908 may therefore lengthen the duration over which process 900 can be continuously executed. In some cases, process 900 can be executed indefinitely and/or for a continuous period of at least several days.

Figure 10:
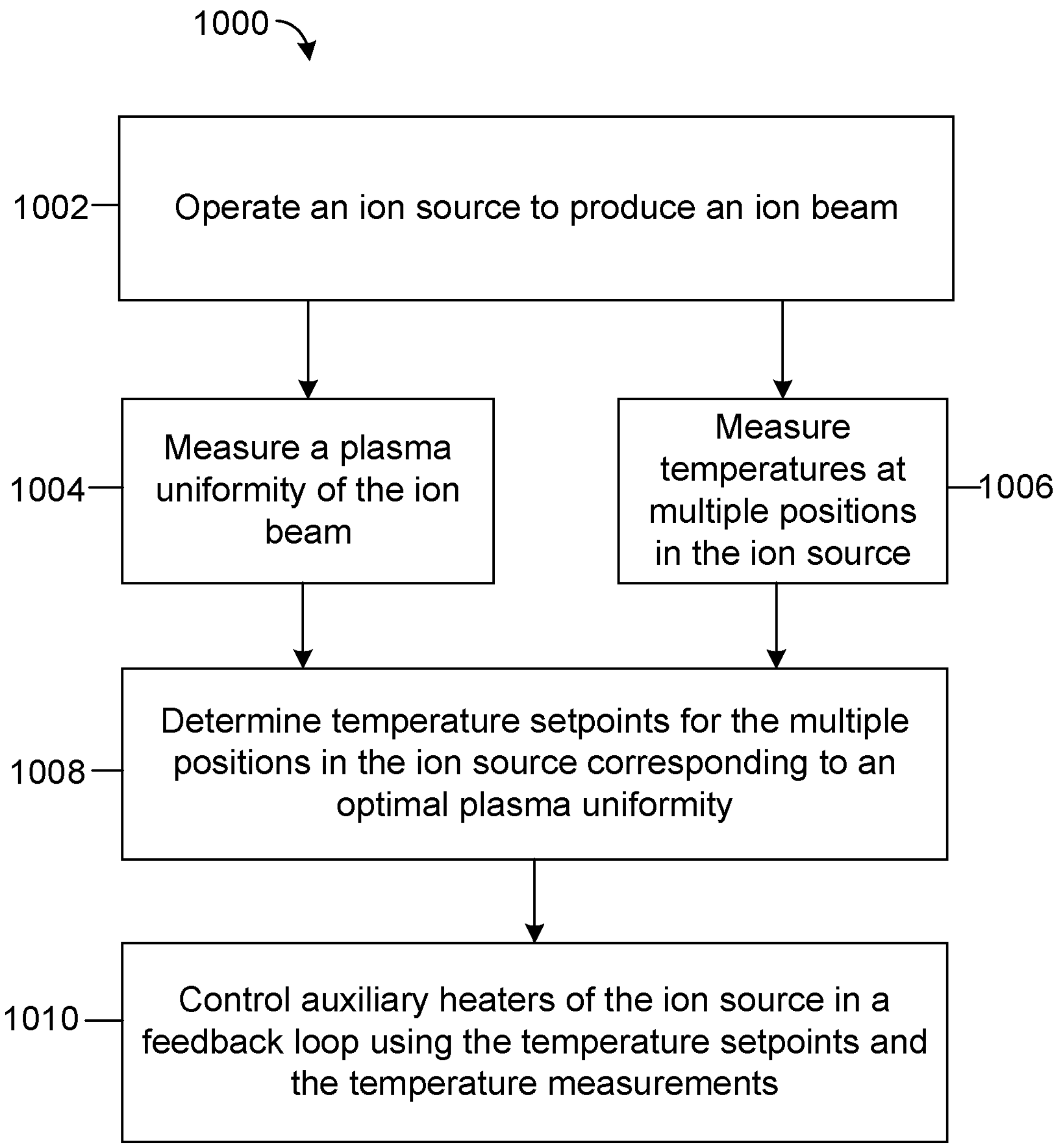
FIG. 10 is a flowchart of a process for controlling an ion source, according to an example embodiment.

Referring now to FIG. 10, a flowchart of a process 1000 for controlling the auxiliary heaters of an ion source is shown, according to an exemplary embodiment. The process 1000 can be executed with regards to the ion source 100 described above, for example, or for some other ion source. The process 1000 can be executed by the control system 300 of FIG. 3, and/or as part of configuring the control loop 200 of FIG. 2, in some embodiments.

At step 1002, an ion source is operated to produce an ion beam. For example, step 1002 can correspond to process 900. For example, a metallic gas can be ionized in a Bernas ion source and the ions can be extracted from the ion source as a beam emitted from an aperture of the ion source.

At step 1004, a plasma uniformity of the ion beam is measured. For example, a beam analyzer device can be provided which can directly measure a plasma uniformity of the ion beam. The beam analyzer device may interrupt or prevent operation of other down-stream processing stages for the ion beam, such that step 1004 relates to a startup (configuration, calibration, testing, training) phase for the ion source. Multiple measurements of the plasma uniformity can be collected and stored over time, for example at controller 302 of FIG. 3, or in some other computer-readable media.

At step 1006, temperatures are measured at multiple positions in the ion source. Step 1006 can be executed concurrently with step 1004. Step 1006 can include receiving measurements from temperature sensors (e.g., thermocouples) 124 which are positioned at multiple positions in the chamber 102 of the ion source 100. Each temperature measurement is associated with a particular sensor and/or position and a time of collection, so that the sample of temperature measurements for a particular time can be associated with the plasma uniformity measured at that particular time.

Steps 1004 and 1006 can be executed concurrently for a sufficient duration of time to collect a robust data set which includes, for each of multiple time steps, a set of multiple temperature measurements for multiple positions in the ion sources for the time step and a measurement of the plasma uniformity of the ion beam for the time step. In some embodiments, a training experiment is executed while steps 1004 and 1006 are executed in which the auxiliary heaters are controlled to cause a wide range of fluctuations in the temperature measurements at the multiple positions, for example so that the data captured in steps 1004 and 1006 include samples that span the entire operating capacity of the auxiliary heaters. It should be expected that the experiment would result in corresponding changes to the plasma uniformity as an effect of the varying temperatures.

At step 1008, temperature setpoints for the multiple positions in the ion source (e.g., for the multiple temperature sensors) that correspond to optimal plasma uniformity are determined. For example, the set of data collected in steps 1004 and 1006 can be searched to find the best plasma uniformity measured during data collection, and the measured temperatures for the corresponding time step can be selected as the temperature setpoints. As another example, a machine-learning, neural network, regression, optimization, numerical analysis, or other modeling or data processing approach can be used to determine the optimal temperature setpoints for generating an ion beam with optimal plasma uniformity based on data collected in steps 1004 and 1006.

In other embodiments, steps 1004, 1006, and 1008 are executed concurrently and step 1008 includes controlling the one or more heaters to seek an optimal (best, extremum, maximum) measured plasma uniformity. In such an embodiment, operation of the one or more heaters is adjusted until the optimal plasma uniformity is being measured by the beam analyzer. Once this optimal state is achieved, the current settings for the one or more heaters can be determined as the optimal settings of the one or more heaters. For example, an amount of power provided to the one or more heaters in that state can be determined as the optimal setting for the one or more heaters and used for online control of the one or more heaters. As another example, the temperatures measured by sensors 124 at various positions in the chamber 102 when the ion source has been tuned to produce an ion beam with optimal plasma uniformity can be determined as the temperature setpoints for use in online control of the one or more heaters.

At step 1010, the auxiliary heaters are controlled in a feedback loop using the temperature setpoints determined in step 1008 and temperature measurements from the ion source. For example, a control loop 200 as in FIG. 2 can be used. Step 1010 can correspond to online operation of the ion source to produce an ion beam used in downstream processing steps for the ion beam. The training stage of steps 1002, 1004, 1006, and 1008 is such that online control of the one or more auxiliary heaters in step 1010 provides the ion beam with the optimal plasma uniformity that can be achieved by the ion source.

Although step 1010 is focused on temperature values and measurements of a plasma uniformity, process 1000 can be adapted to account for additional or other inputs (e.g., settings for or measurements relating to operation of the oven 112, filament 116, reflector electrode 118, extraction devices, etc.) or outputs (e.g., other properties of the ion beam) and to train control logic for various elements of the control system 300. All such variations are within the scope of the present disclosure.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical values or idealized geometric forms provided. Accordingly, these terms should be interpreted as indicating that insubstantial or inconsequential modifications or alterations of the subject matter described and claimed are considered to be within the scope of the disclosure as recited in the appended claims.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

What is claimed is:

1. An ion source comprising:

a chamber having a first end, a second end opposite the first end, a first wall extending from the first end to the second end, and a second wall opposite the first wall;

a source filament at the first end of the chamber and configured to emit electrons and a first amount of heat;

a beam aperture at the second wall of the chamber; and one or more heaters positioned within the chamber and between the second end and the beam aperture and operable to provide a second amount of heat;

wherein the one or more heaters are positioned and operable such that the second amount of heat balances the first amount of heat to reduce or eliminate a temperature gradient in the chamber.

2. The ion source of claim 1, further comprising:

a plurality of thermocouples distributed in the chamber; and a controller configured to provide closed-loop control of the one or more heaters based on output from the plurality of thermocouples.

3. The ion source of claim 1, further comprising a reflector electrode at the second end of the chamber and configured to reflect the electrons away from the second end.

4. The ion source of claim 3, wherein operation of the one or more heaters reduces or eliminates condensation on an insulator of the reflector electrode.

5. The ion source of claim 1, further comprising a gas inlet at the second wall of the chamber, wherein the gas inlet is aligned with the beam aperture.

6. The ion source of claim 1, wherein the one or more heaters comprise a first cylindrical heater extending from the second end of the chamber and along the first wall of the chamber.

7. The ion source of claim 6, wherein the one or more heaters comprise a second cylindrical heater extending from the second end of the chamber and along the first wall of the chamber, wherein the second cylindrical heater is spaced apart from the first cylindrical heater.

8. The ion source of claim 1, further comprising a plurality of support posts coupled to the first wall of the chamber and extending away from the chamber, wherein the plurality of support posts provide uniform pathways for heat transfer out of the chamber.

9. The ion source of claim 8, further comprising a water-cooling system, wherein:

the plurality of support posts extend from the chamber to the water-cooling system; and the water-cooling system is configured to remove heat from the plurality of support posts.

10. The ion source of claim 9, wherein the water-cooling system is further configured to measure the heat removed from the plurality of support posts by the water-cooling system.

11. The ion source of claim 1, further comprising an oven configured to provide an Ytterbium gas into the chamber via an inlet in the first wall.

12. The ion source of claim 1, further comprising a test device configured to measure a plasma uniformity of an ion beam emitted from the beam aperture, wherein control for the one or more heaters is tuned based on the plasma uniformity.

13. The ion source of claim 1, wherein the second amount of heat is substantially equal to the first amount of heat.

14. The ion source of claim 1, wherein reducing or eliminating the temperature gradient in the chamber causes a reduction or elimination of a non-uniform current in an ion beam emitted from the beam aperture.

15. A method, comprising:

providing a metallic gas into a chamber;

ionizing the metallic gas by providing power to a filament to cause the filament to emit electrons in the chamber, wherein providing power to the filament causes the filament to add heat to the chamber proximate a first end of the chamber;

reducing or eliminating a temperature gradient in the chamber by operating one or more heaters positioned in the chamber, the one or more heaters positioned inside the chamber and extending from a second end of the chamber opposite the first end; and extracting an ion beam from the chamber via an aperture positioned between the filament and the one or more heaters.

16. The method of claim 15, wherein operating the one or more heaters comprises causing the one or more heaters to balance the heat added to the chamber by the filament.

17. The method of claim 15, further comprising measuring temperatures at a plurality of positions in the chamber; and wherein operating the one or more heaters comprises controlling the one or more heaters based on the temperatures at the plurality of positions in the chamber.

18. The method of claim 17, further comprising:

measuring a plasma uniformity of the ion beam extracted through the aperture; and determining setpoints for the temperatures at the plurality of positions in the chamber based on measurements of the plasma uniformity, wherein the setpoints are associated with optimal plasma uniformity.

19. The method of claim 18, comprising controlling the one or more heaters to drive the temperatures at the plurality of positions to the setpoints.

20. The method of claim 15, further comprising removing heat from the chamber by operating a water cooling system thermally coupled to the chamber by a plurality of support posts.

* * * * *